(12) United States Patent
Reinschke (10) Patent No.: US 8,475,363 B2
(45) Date of Patent: Jul. 2, 2013

(54) COIL ARRANGEMENT FOR GUIDING A MAGNETIC ELEMENT IN A WORKING SPACE

(75) Inventor: Johannes Reinschke, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 288 days.

(21) Appl. No.: 12/863,247

(22) PCT Filed: Dec. 29, 2008

(86) PCT No.: PCT/EP2008/068312
§ 371 (c)(1),
(2), (4) Date: Jul. 16, 2010

(87) PCT Pub. No.: WO2009/089992
PCT Pub. Date: Jul. 23, 2009

(65) Prior Publication Data
US 2011/0054254 A1    Mar. 3, 2011

(30) Foreign Application Priority Data
Jan. 17, 2008   (DE) .......................... 10 2008 004 871

(51) Int. Cl.
*A61B 1/00*    (2006.01)
*H01F 5/00*    (2006.01)

(52) U.S. Cl.
USPC ........................................... 600/118; 335/299

(58) Field of Classification Search
USPC ................... 335/299; 600/117–118
See application file for complete search history.

(56) References Cited

U.S. PATENT DOCUMENTS

| 5,931,818 | A | 8/1999 | Werp et al. |
|---|---|---|---|
| 6,015,414 | A | 1/2000 | Werp et al. |
| 6,241,671 | B1 * | 6/2001 | Ritter et al. .................. 600/427 |
| 2005/0052178 | A1 | 3/2005 | Ries |
| 2008/0272873 | A1 | 11/2008 | Reinschke et al. |

* cited by examiner

*Primary Examiner* — Ramon Barrera
(74) *Attorney, Agent, or Firm* — Schiff Hardin LLP (57) ABSTRACT

A coil arrangement for contact-free guidance of a magnetic element such as an endoscopy capsule, has a number of individual coils arranged in pairs by which the components of a guidance field are generated. By arranging the individual coils to include coils corresponding to blades at an exterior of a cylindrical surface, the number of degrees of freedom required for guidance can be obtained with fewer individual coils and fewer power amplifiers to operate the coils.

34 Claims, 9 Drawing Sheets

COIL ARRANGEMENT FOR GUIDING A MAGNETIC ELEMENT IN A WORKING SPACE

This application is a continuation application of International Application No. PCT/EP2008/068312, filed on Dec. 29, 2008

BACKGROUND OF THE INVENTION

1. Field of the Invention

The invention concerns a coil arrangement for contactless guidance of a magnetic element—in particular an endoscopy capsule—in a work space (cooperating space).

2. Description of the Prior Art

The use of endoscopes and catheters is increasingly widely applied in medicine for the diagnosis or the treatment of the inside of a patient. The instruments are introduced into the body via bodily orifices or cuts in the body and can be displaced in a longitudinal direction, directed from the outside, for which a mechanical connection to the instrument is necessary. However, given the forward movement of the instrument into the body, difficulties in the navigation normally occur at curves or branches, in the manner that the operator must direct the instrument in the desired direction, possibly via repeated testing, and a supporting force from the tissue on the instrument is required for the further navigation. This is linked with a large time cost for the operator and with pain for the patient. In the worst case, it is not to be precluded that the guidance in the planned direction is not achieved at all, or that the risk of tissue perforation arises. Furthermore, in the case of endoscopy it can be of interest to rotate the endoscopy head equipped with a camera in specific directions, for example in order to completely view the mucous membrane in a segment of the gastrointestinal tract. With current catheter endoscopes this is only conditionally possible because the catheter tip has only limited mobility. Moreover, typical catheter endoscopes have the disadvantage that remotely situated internal organs can only be reached with difficulty, or cannot be reached at all.

The passive endoscopy capsule moved via the natural peristalsis of the gastrointestinal tract does not have the cited disadvantages, but also cannot be navigated, which means that the targeted viewing of specific points inside the gastrointestinal tract is not possible. Therefore, magnetic navigation or guidance systems have been proposed that enable a catheterless or wireless guidance of endoscopy capsules that contain a magnetic dipole moment. A catheterless or wireless guidance is also designated as "contactless" in the following.

DE 103 40 925 B3 and WO 2006/092421 A1 respectively describe a magnetic coil arrangement consisting of 14 individual coils for navigation of an endoscopy capsule, a video capsule or another probe. The capsule is hereby equipped with a magnetic element, for example a permanent magnet or ferromagnet. The magnetic coil arrangement generates magnetic field components $B_x$, $B_y$, $B_z$ along the axes x, y, z of a Cartesian coordinate system, as well as magnetic gradient fields that enable a contactless guidance of the endoscopy capsule.

Use is made of the fact that the magnetic element—i.e. a body with a magnetic dipole moment $\vec{m}$—seeks to align parallel to the direction of the magnetic field $\vec{B}$ consisting of the magnetic field components $B_x$, $B_y$, $B_z$ in the direction of the axes of the Cartesian coordinate system. Since the magnetic element is firmly connected with the endoscopy capsule, the orientation of the capsule can thus be affected. A force $\vec{F} = G \cdot \vec{m}$ with a gradient matrix G comprising the gradient fields, triggered by the magnetic gradient fields $\partial B_x / \partial x$ etc., additionally acts on the magnetic dipole moment $\vec{m}$ according to $$\vec{F} = \underline{\underline{G}} \cdot \vec{m} = \begin{pmatrix} \frac{\partial B_x}{\partial x} & \frac{\partial B_x}{\partial y} & \frac{\partial B_x}{\partial z} \\ \frac{\partial B_y}{\partial x} & \frac{\partial B_y}{\partial y} & \frac{\partial B_y}{\partial z} \\ \frac{\partial B_z}{\partial x} & \frac{\partial B_z}{\partial y} & \frac{\partial B_z}{\partial z} \end{pmatrix} \cdot \vec{m}.$$

The gradient matrix G is symmetrical and trace-free due to the Maxwell equations $\text{rot}\vec{B}=0$ and $\text{div}\vec{B}=0$, meaning that with $\partial B_x/\partial y$ ($=\partial B_y/\partial x$), $\partial B_x/\partial z$ ($=\partial B_z/\partial x$), $\partial B_y/\partial z$ ($=\partial B_z/\partial y$) and two of the three diagonal elements (for example $\partial B_x/\partial x$ and $\partial B_y/\partial y$) it contains five independent gradient fields.

The magnetic field $\vec{B}$ and the gradient fields can be set arbitrarily via a targeted activation of the individual coils of the magnetic coil arrangement. It is therefore possible to rotate the magnetic element and thus to position it arbitrarily in a work space A within the magnetic coil arrangement. It is possible to exert a force $\vec{F}$ on the magnetic element in order to shift it translationally in addition to the rotation. For this eight quasi-static magnetic degrees of freedom are realized, namely the magnetic field components $B_x$, $B_y$, $B_z$ as well as two of the three entries of the diagonal elements (for example $\partial B_x/\partial x$ and $\partial B_y/\partial y$) and three of the secondary diagonal elements (for example $\partial B_x/\partial y$ $\partial B_z/\partial x$, $\partial B_z/\partial y$) of the gradient matrix G.

The systems described in DE 103 40 925 B3 and WO 2006/092421 A1 have the disadvantage that, because of the 14 individually activated coils that are required there, they are relatively cost-intensive in their manufacture and installation due to the high number of coils and power amplifiers.

SUMMARY OF THE INVENTION

An object of the invention to provide a more cost-effective magnetic guidance system that includes a coil arrangement and multiple power amplifiers associated with the coils.

The present invention assumes that only a limited number of maneuvers of an endoscopy capsule is required for the examination of a patient, thus that the design of a coil arrangement is to be optimized with regard to these maneuvers that are actually necessary. In particular, a markedly more cost-effective design is achieved via a detailed analysis of the requirements of the coil arrangement and a design of the individual coils such that only the field strengths and field gradients that are required in the consideration of the desired maneuvers of the endoscopy capsule must be able to be realized in a directionally selective manner.

In the design of the coil arrangement it is assumed that a permanent magnet is firmly installed in the endoscopy capsule. The permanent magnet is thus firmly connected with the capsule so that movements of the permanent magnet that are triggered by the coil arrangement according to the invention are transferred to the endoscopy capsule. The magnetic moment $\vec{m}$ of the permanent magnet is preferably oriented either in the direction of the longitudinal axis of the capsule or perpendicular to this. Depending on these two possibilities of the permanent magnet alignment, slight differences result in the magnetic guidance system according to the invention.

The optimization with regard to the actual required maneuvers of the endoscopy capsule—which is described in the following in connection with Figures in the example of an examination of the esophagus, the stomach (gaster) and the duodenum (what is known as an "EGD" examination)—leads to a coil arrangement to guide the endoscopy capsule with only ten or twelve individual coils. A few of the ten or twelve individual coils are thereby operated in pairs, i.e. via the same power amplifier. This is advantageously reflected in that only six, seven or eight power amplifiers are required.

The fundamental mode of operation of the coil arrangement according to the invention is analogous to the mode of operation of the arrangement described in DE 103 40 925 B3 or, respectively, in WO 2006/092421 A1. Therefore, reference is made to DE 103 40 925 B3 and WO 2006/092421 A1 with regard to this and with regard to theoretical foundations.

The coil arrangement according to the invention advantageously allows that the same number of magnetic degrees of freedom (maximum of eight) relative to the arrangements described in DE 103 40 925 B3 or, respectively, in WO 2006/092421 A1 can be generated via an altered layout of the coil arrangement with fewer individual coils and fewer power amplifiers. If, due to a particular application or, respectively, examination, one or more of these degrees of freedom is not necessary, the coil arrangement can make do with fewer power amplifiers or possibly also with fewer coils as well.

DESCRIPTION OF THE PREFERRED EMBODIMENTS

First Exemplary Embodiment

Figure 1:
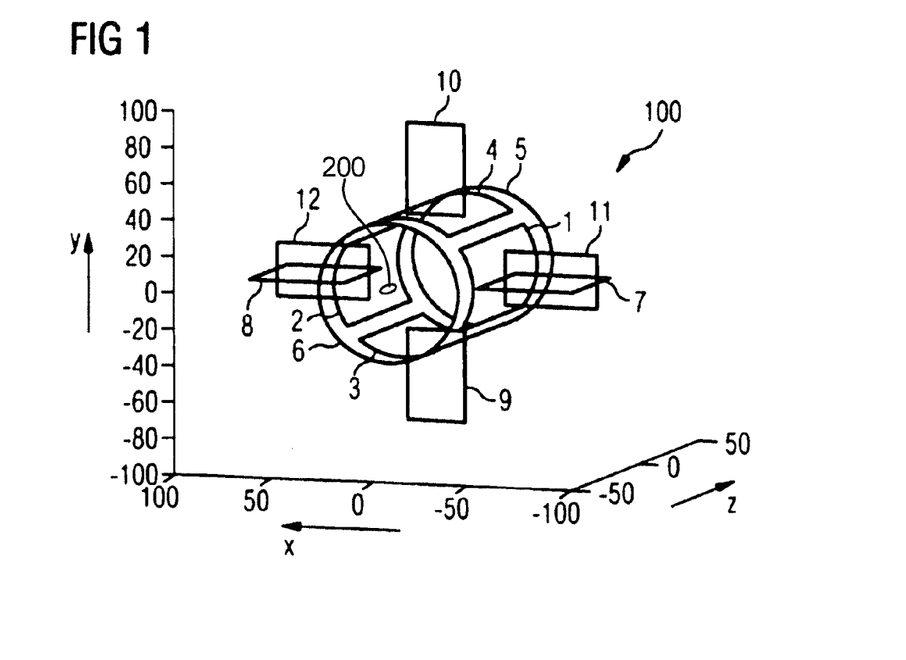
FIG. 1 schematically illustrates an exemplary embodiment of a coil arrangement according to the present invention.

FIG. 1 shows a coil arrangement 100 according to the invention that is provided to guide or, respectively, navigate a magnetic element—in particular an endoscopy capsule 200—inside a patient (not shown), which magnetic element contains a permanent magnet with a magnetic dipole moment $\vec{m}$ in the direction of the longitudinal axis of the capsule 200. The permanent magnet is firmly connected with the endoscopy capsule 200 so that movements of the permanent magnet that are generated by the coil arrangement 100 are transferred directly to the endoscopy capsule 200. In particular, the coil arrangement 100 can generate magnetic field components $B_x$, $B_y$, $B_z$, as well as specific gradient fields ($\partial B_x/\partial x$ etc.) of the gradient matrix G that are defined in a Cartesian coordinate system x, y, z (as shown in FIG. 1). The longitudinal axis of the coil arrangement 100 corresponds to the z-axis of the coordinate system. This definition of the coordinate system also applies in the same form to the further exemplary embodiments.

In contrast to the coil arrangements described in DE 103 40 925 B3 and WO 2006/092421 A1 with fourteen individual coils, the coil arrangement 100 of the first exemplary embodiment contains only twelve individual coils 1-12, comprising a first coil 1 through twelfth coil 12.

Four of the twelve individual coils 1-12 (in particular the first coil 1 through fourth coil 4) of the circuit arrangement 100 are fashioned as identically shaped saddle coils 1-4 and comprise a work space A in which the patient is positioned. The saddle coils 1-4 form an (imaginary) surface shell of a cylinder with circular cross section and extend along the periphery of the surface shell, respectively over the same solid angle $\alpha_1=\alpha_2$ (see FIG. 5A). The center of the cylinder is located at the origin of the Cartesian coordinate system; the longitudinal axis or, respectively, axis of symmetry of the cylinder is oriented in the z-direction. The saddle coils 1-4 are advantageously arranged spaced apart from one another as viewed in the circumferential direction of the surface shell, meaning that an interstice that permits a thermal expansion of the saddle coils is respectively located between their facing side segments (and thus between their longitudinal sides running in the z-direction). The first saddle coils 1, 2 form a first coil pair 1, 2 and the second saddle coils 3, 4 form a second coil pair 3, 4.

The fifth coil 5 and the sixth coil 6 form the termination of the cylinder in the z-direction and are fashioned as ring coils, meaning that the individual coils 5, 6 are flat, circular coils and possess a rectangular cross section. The ring coils 5, 6 respectively lie in a plane parallel to the x-y plane and form a third coil pair 5, 6. As viewed in the z-direction, the coil pairs 5, 6 are located at positions $+z_r$ and $-z_r$, for example with $z_r=400$ mm. The center points of the ring coils 5, 6 lie on the z-axis; the inner diameters of the ring coils 5, 6 correspond to the inner diameter $d_M$ of the surface shell formed by the saddle coils 1-4, wherein $d_M=620$ mm can apply, for example. The length of the surface shell in the z-direction is defined by the length of the saddle coils 1-4 in the z-direction. According to FIG. 5B, a saddle coil can be 700 mm long, for example.

The saddle coils 1-4 and/or the ring coils 5, 6 can alternatively be designed as surface coils. The position of the respective coils in the coordinate system that is described above can thereby remain unchanged. Surface coils are characterized in that they are fashioned as flat coils (for example in contrast to saddle coils) and advantageously exhibit a rectangular cross section.

Six additional individual coils 7-12, in particular the seventh coil 7 through twelfth coil 12 [sic], are arranged like blades and are fashioned as rectangular surface coils 7-12, wherein the sides of the respective rectangle are aligned parallel to the corresponding axes of the coordinate system. The term "like blades" thereby designates that the respective individual coil is simultaneously arranged radially outside of the surface shell of the cylinder formed by the saddle coils 1-4 in the x-y-plane, in the x-z-plane or in they-z-plane, as is apparent in FIG. 1.

In principle it applies that the individual coils 1-12 should be placed optimally close to the work space A. The surface coils 7-12 are specifically dimensioned such that they are markedly more flat than wide as viewed from the coordinate origin.

The first surface coils 7, 8 are located in the x-z-plane, i.e. in the y-direction at positions y=0, and form a fourth coil pair 7, 8. The radially inner conductive sections of the first surface coils 7, 8 are located at positions $+r_f$ and $-r_f$ in the x-direction, wherein $2r_f=840$ mm, for example. The first surface coils 7, 8 are positioned in the z-direction such that their geometric center points lie at z=0.

The second surface coils 9, 10 are located in the x-y-plane, i.e. in the z-direction at positions z=0, and form a fifth coil pair 9, 10. The radially inner conductive sections of the second surface coils 9, 10 are located at positions $+r_f$ and $-r_f$ in the y-direction. The second surface coils 9, 10 are positioned in the x-direction such that their geometric center points lie at x=0.

Furthermore, third surface coils 11, 12 are provided that form a sixth coil pair 11, 12. The surface coils 11, 12 are located in the x-y-plane, i.e. in the z-direction at positions z=0, and are crossed at the first surface coils 7, 8 and arranged within the first surface coils 7, 8. The radially inner conductive sections of the additional surface coils 11, 12 are located at positions $+r_f$ and $-r_f$ in the x-direction. The additional surface coils 11, 12 are positioned in the y-direction such that their geometric center points lie at y=0.

A coil pair, i.e. a saddle coil pair, a ring coil pair or, respectively, a surface coil pair, is characterized in that the two individual coils associated with the coil pair are point-symmetrical to one another relative to the origin of the Cartesian coordinate system (x, y, z). The line connecting the geometric center points of the coils of a coil pair passes through the origin of the coordinate system. It additionally applies—in particular for a saddle coil pair and a ring coil pair—that the respective line connecting the geometric center points of the coils of these coil pairs is perpendicular to the cross sectional surface of the coils. What is thereby to be understood by the cross sectional surface of a saddle coil is the surface that is defined by the two conductive segments running in the z-direction. For example, according to FIG. 5*b* the cross sectional surface of the saddle coil 4 would accordingly lie in a plane parallel to the y-z-plane. The two individual coils associated with a coil pair can possibly be fed with current by a common power amplifier instead of respectively supplying the two individual coils with current via separate power amplifiers.

Figure 2A:
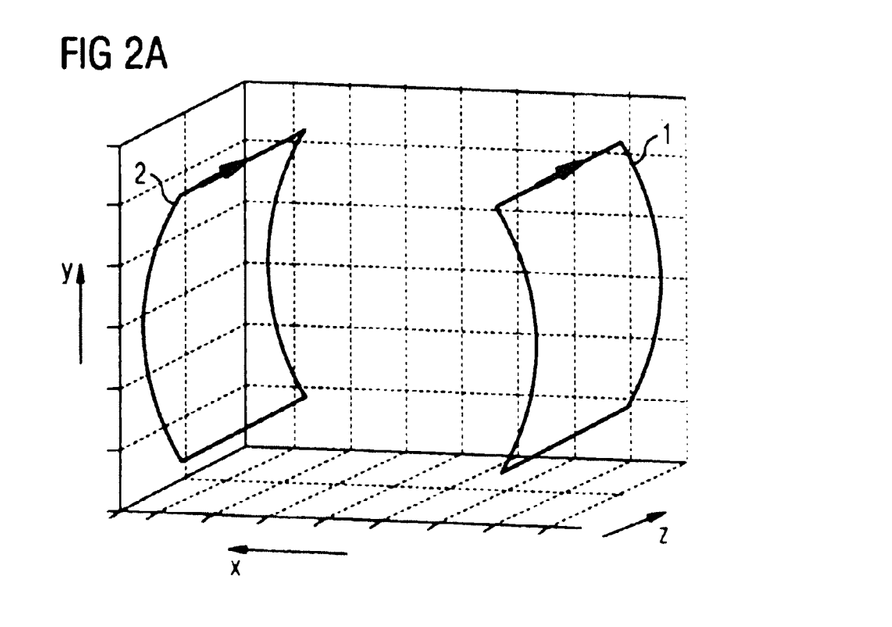
FIG. 2 schematically illustrates different coil pairs of the coil arrangement in accordance with the present invention, with identification of current flow through the coil pairs.
Figure 2B:
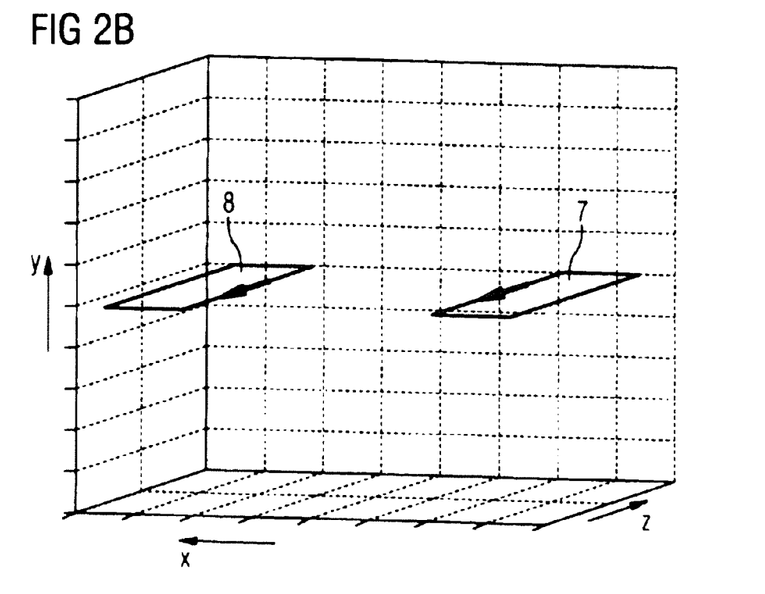
Figure 2C:
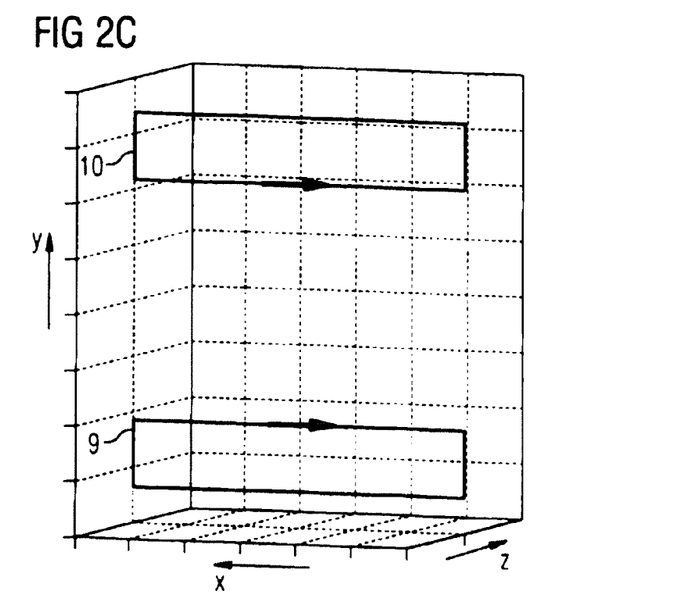

FIGS. 2A-2C show the current flow through the coil pairs 1 and 2 (FIG. 2A), 7 and 8 (FIG. 2B) and 9 and 10 (FIG. 2C), wherein the direction of the current is symbolized by arrows. These three coil pairs are respectively operated by only one power amplifier. With this the coil pair 1, 2 generates the component $B_x$ of the magnetic field $\vec{B}$. The coil pair 7, 8 is used to generate the gradient field $\partial B_y/\partial x$ ($=\partial B_x/\partial y$) and the coil pair 9, 10 generates the gradient field $\partial B_z/\partial y$.

In contrast to the coil pairs described above in connection with FIGS. 2A-2C, the coils 3 through 6 are operated individually by separate power amplifiers and on the one hand generate the component $B_y$ (individual coils 3, 4) and $B_z$ (individual coils 5, 6) of the magnetic field $\vec{B}$. On the other hand, the gradient fields $\partial B_y/\partial y$ and $\partial B_z/\partial z$ are generated in that the individual coils 3 and 4 are supplied with different currents to generate the gradient field $\partial B_y/\partial y$. The gradient field $\partial B_z/\partial z$ is accordingly constructed via different currents in the individual coils 5 and 6.

The surface coils 11, 12 are operated by a common power amplifier and generate a gradient field $\partial B_z/\partial x$.

With the coil arrangement 100 of the first exemplary embodiment it is accordingly possible to realize all eight magnetic degrees of freedom—i.e. the magnetic field components $B_x$, $B_y$, $B_z$ and the five gradient fields $\partial B_y/\partial y$, $\partial B_z/\partial z$, $\partial B_x/\partial y$, $\partial B_z/\partial x$, $\partial B_z/\partial y$ of the gradient matrix $\overline{\overline{G}}$—with only twelve individual coils and eight power amplifiers.

The coil arrangement 100 of the first exemplary embodiment is executed rigid, meaning that the individual coils 1-12 are mechanically immobile and no permanent magnets are provided. The same applies for the coil arrangements of the additional exemplary embodiments.

Before the description of additional exemplary embodiments, in the following the further optimization with regard to the actual required maneuvers of the endoscopy capsule is described.

A limited number of maneuvers M1-M5 of the endoscopy capsule 200 are necessary for a complete examination of the esophagus, the stomach (gaster) and the duodenum of the patient. The coil arrangement 100 can accordingly be designed for the specific application according to FIGS. 3A, 3B, 8 and 9. The patient is typically located inside the coil arrangement 100, lying on his back or on his stomach with the longitudinal axis of the body in the z-direction.

M1: To examine the esophagus, the endoscopy capsule 200 merely needs to be moved in the z-direction since the esophagus is also oriented in the z-direction to a good approximation. A force in the z-direction must accordingly be generated. The coil arrangement must accordingly construct a gradient field $\partial B_z/\partial z$.

M2: For the navigation of the capsule 200 in the stomach it is required that it is partially filled with fluid. For this the patient must take water before and during the examination. In order to maneuver the endoscopy capsule (which is aligned in the y-direction) on the water's surface with permanent magnets magnetized in the longitudinal direction of the capsule, i.e. in the x-direction and/or z-direction, gradient fields $\partial B_y/\partial x$ ($=\partial B_x/\partial y$) and $\partial B_y/\partial z$ ($=\partial B_z/\partial y$) are necessary. The expressions placed in parentheses inevitably result due to the Maxwell Equation $\mathrm{rot}\vec{B}=0$.

M3: In order to hold the position of the endoscopy capsule 200 on the water's surface in the stomach, a magnetic force must be generated that counteracts the force of gravity. It is thereby again assumed that the magnetic moment $\vec{m}$ of the endoscopy capsule 200 is oriented in the y-direction. A gradient field $\partial B_y/\partial y$ must accordingly be generated. This can moreover by used in order to let the endoscopy capsule 200 submerge and surface again.

M4: For the acquisition of images of the inner stomach wall, for example, it can be necessary to rotate the endoscopy capsule 200 in a specific, arbitrary direction $\vec{r}$. For this the coil arrangement 100 must construct a magnetic field $\vec{B}$ parallel to the desired direction $\vec{r}$. It must accordingly be possible to generate all components $B_x$, $B_y$, $B_z$ of the magnetic field $\vec{B}$.

M5: In order to direct the endoscopy capsule 200 (which furthermore is essentially oriented in the y-direction) through the pyloric orifice, a gradient field $\partial B_y/\partial y$ is necessary again.

Second Exemplary Embodiment

Figure 3A:
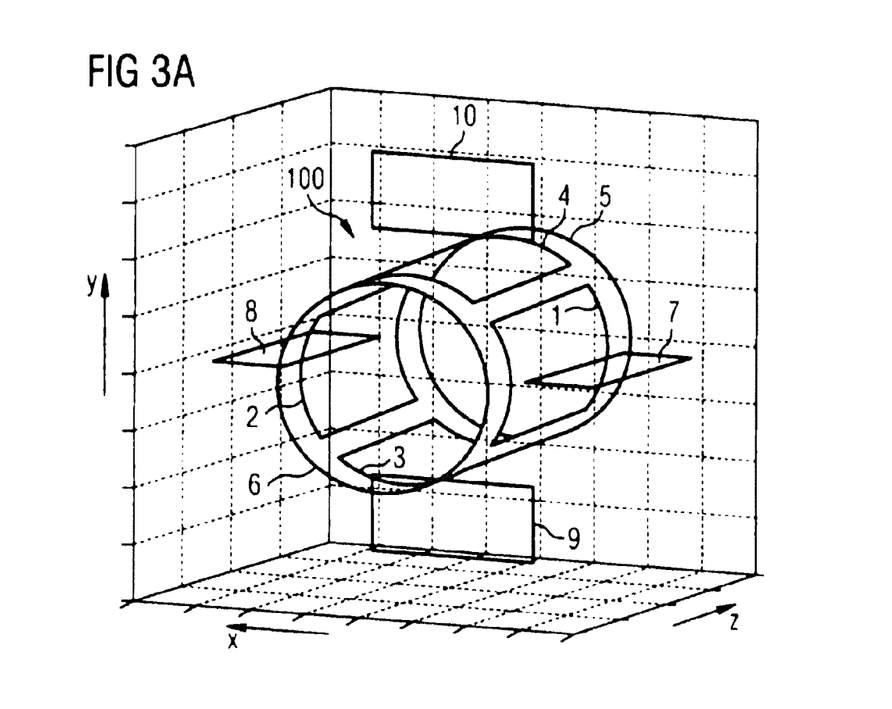
FIG. 3A schematically illustrates a further exemplary embodiment of the coil arrangement according to the invention.
Figure 3B:
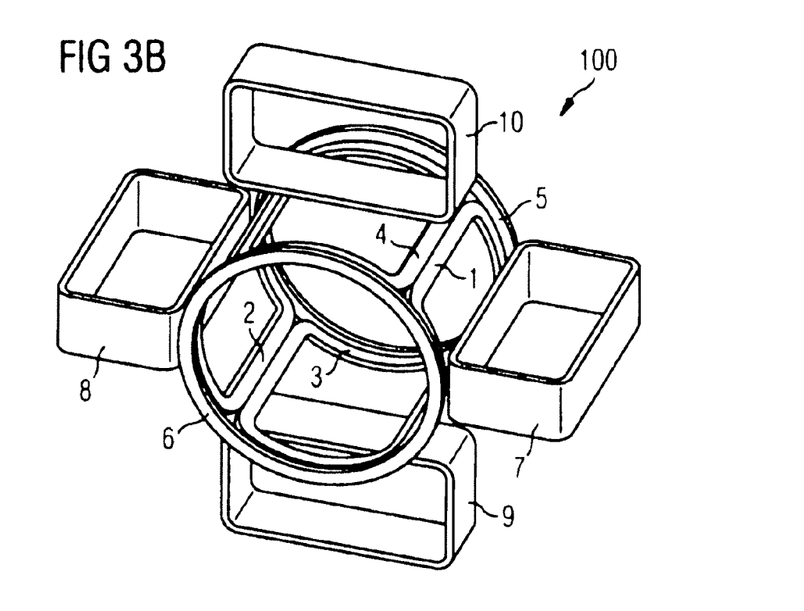
FIG. 3B is a perspective view of the exemplary embodiment of FIG. 3A.

In a second exemplary embodiment, the coil arrangement 100 shown in FIGS. 3A-3B is used to navigate the endoscopy capsule 200 in the stomach of the patient. For this it can be assumed that the endoscopy capsule 200 was conveyed into the stomach via the normal swallowing process. The maneuvers M2 through M4 listed above are necessary to maneuver the capsule 200 in the stomach. The coil arrangement 100 of the first exemplary embodiment must accordingly generate a magnetic field $\vec{B}$ in an arbitrary direction as well as the gradient fields $\partial B_y/\partial y$, $\partial B_y/\partial x$ and $\partial B_z/\partial y$. In comparison to the first exemplary embodiment, it is accordingly not necessary to generate a gradient field $\partial B_z/\partial x$. The third surface coils 11, 12 can therefore be omitted, such that in the second exemplary embodiment only ten individual coils 1-10, i.e. the first coil 1 through tenth coil 10, are necessary.

Moreover, in a second exemplary embodiment only six power amplifiers are required to generate the cited magnetic field components and gradient fields: the four coil pairs consisting of the individual coils 1 and 2, 5 and 6, 7 and 8 and 9 and 10 are respectively supplied via a common power amplifier and generate the magnetic field components or gradient fields $B_x$, $B_z$, $\partial B_y/\partial x$ and $\partial B_z/\partial y$. The individual coils 3 and 4 are operated with different currents (and therefore with two individual power amplifiers) to generate the magnetic field component $B_y$ and the gradient field $\partial B_y/\partial y$.

Figure 3C:
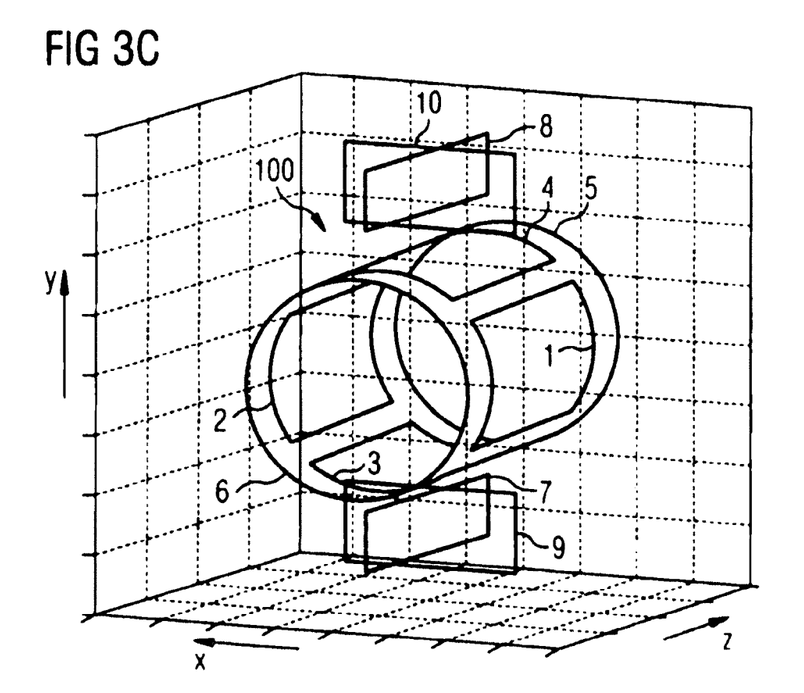
FIG. 3C shows an alternative arrangement for the exemplary embodiment of FIG. 3A.

Since the gradient matrix $\underline{G}$ is symmetrical, as described above, $\partial B_y/\partial x = \partial B_x/\partial y$ applies. Instead of the positioning of the individual coils 7, 8 that is shown in FIG. 3A for the generation of the gradient field $\partial B_y/\partial x$, the individual coils 7, 8 can be arranged crossed with 9, 10 (as shown in FIG. 3c) for the generation of a gradient field $\partial B_x/\partial y$. The coil pair 7, 8 is thereby furthermore supplied via a common power amplifier. The surface coils 7, 8 are now located in the y-z plane, i.e. in the x-direction at positions x=0. In the z-direction the first surface coils 7, 8 are positioned such that their geometric center points lie at z=0.

Third Exemplary Embodiment

The coil arrangement 100 in the third exemplary embodiment is provided to guide the endoscopy capsule 200—which is magnetized parallel to its longitudinal axis—through the esophagus, the stomach (gaster) an the duodenum of the patient, i.e. for a complete EGD examination. All of the maneuvers M1 through M5 that are listed above are accordingly to be realized in the third exemplary embodiment.

The coil arrangement 100 must accordingly be fashioned such that a magnetic field $\vec{B}$ in an arbitrary direction as well as gradient fields $\partial B_y/\partial y$, $\partial B_x/\partial z$, $\partial B_y/\partial x$ and $\partial B_z/\partial y$ can be generated. For this ten individual coils 1-10 are necessary, as in the second exemplary embodiment. However, in contrast to the second exemplary embodiment seven power amplifiers are required: the three coil pairs consisting of the first coil 1 and the second coil 2, the seventh coil 7 and the eighth coil 8 and the ninth coil 9 and the tenth coil 10 are respectively operated via one power amplifier and generate the fields or, respectively, gradient fields $B_x$, $\partial B_y/\partial x$ and $\partial B_z/\partial y$. The third coil 3 and the fourth coil 4 are operated with different currents (and therefore with two individual power amplifiers) to generate the magnetic field component $B_y$ and the gradient field $\partial B_y/\partial y$. The coils 5 and 6 are likewise operated with two individual power amplifiers to generate $B_z$ and $\partial B_z/\partial z$.

Fourth Exemplary Embodiment

In the fourth exemplary embodiment, the magnetic moment of the permanent magnet of the endoscopy capsule 200 is aligned perpendicular to the longitudinal axis of the endoscopy capsule 200.

In order to implement an examination of the stomach in the second exemplary embodiment, the maneuvers M2' through M4' (that are based on the maneuvers M2 through M4 that are described above) must be executable:

M2': In navigation of the capsule 200 aligned in the vertical direction on the water's surface in the stomach, the magnetic moment $\vec{m}$ of the endoscopy capsule lies in the x-z-plane. In order to maneuver the endoscopy capsule in the x-direction and/or z-direction, gradient fields $\partial B_x/\partial x$ and $\partial B_z/\partial z$ are required.

M3': In order to hold the position of the endoscopy capsule 200 in the stomach at the water's surface, or in order to move the capsule 200 in the vertical direction, gradient fields $\partial B_y/\partial x$ and $\partial B_z/\partial y$ must be generated.

M4': To rotate the endoscopy capsule 200 in a specific, arbitrary direction $\vec{r}$, the coil arrangement 100 must construct a magnetic field $\vec{B}$ parallel to the desired direction $\vec{r}$.

In summary, the magnetic field components $B_x$, $B_x$, $B_x$ and the gradient fields $\partial B_x/\partial x$, $\partial B_z/\partial z$, $\partial B_y/\partial x$ and $\partial B_z/\partial y$ are accordingly required for stomach examination with a diametrally magnetized capsule 200.

To generate these fields, a coil arrangement with ten individual coils 1-10 (as shown in FIGS. 3a/b) can again be used, wherein the three coil pairs (formed by the individual coils 3 and 4, 7 and 8 and 9 and 10) are respectively supplied via a common power amplifier in order to generate the fields or, respectively, gradient fields $B_y$, $\partial B_y/\partial x$ and $\partial B_z/\partial y$. The individual coils 1 and 2 are operated with different currents—and therefore with two individual power amplifiers—to generate the magnetic field component $B_x$ and the gradient field $\partial B_x/\partial x$. The individual coils 5 and 6 are similarly operated with two individual power amplifiers to generate $B_z$ and $\partial B_z/\partial z$. Seven power amplifiers are accordingly required.

Fifth Exemplary Embodiment

The coil arrangement 100 of a fifth exemplary embodiment is identical to the coil arrangement 100 of the first exemplary embodiment and comprises twelve individual coils 1-12 (FIG. 1) and eight power amplifiers. The first exemplary embodiment is referenced regarding the connection of the individual coils 1-12 and the power amplifiers. As is described in connection with the first exemplary embodiment, it is possible with the coil arrangement 100 according to FIG. 1 (which comprises twelve individual coils 1-12) to generate all eight magnetic degrees of freedom. All maneuvers required in connection with the diametrally magnetized endoscopy capsule 200 can accordingly also be implemented. The coil arrangement 100 of the first exemplary embodiment and fifth exemplary embodiment is accordingly universally usable for endoscopy capsules 200 whose magnetic moment $\vec{m}$ is aligned parallel or perpendicular to the longitudinal axis of the capsule. However, differences in the design of the coil arrangement 100 with regard to the current feed of the individual coils and the design of the individual coils (for example with regard to the linkage) result for a diametrally magnetized endoscopy capsule 200 relative to the first exemplary embodiment due to different forces and turning moments to be generated.

Additional Embodiments

Figure 4A:
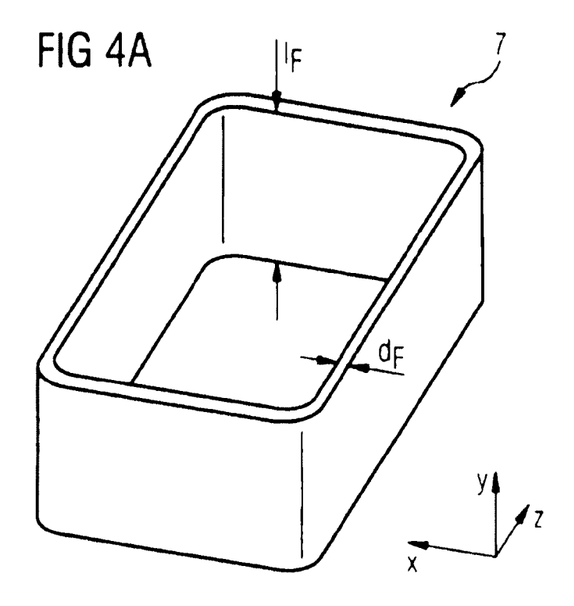
FIG. 4A illustrates a surface coil.

The surface coils 7-12 can be dimensioned such that they are markedly flatter than they are wide as seen from the coordinate origin. The "flat" feature in the example of the surface coil 7 in FIG. 4a thereby concerns the thickness $d_F$ of the conductive segment, i.e. the extent of the inner (and outer) conductive segment as viewed in the x-direction. The "wide" feature describes the extent $l_F$ of the conductive segment in the y-direction. For the surface coil 7 it can accordingly be designed so that $d_F < l_F$ applies. The surface coil 8 can be dimensioned identically. The remaining surface coils 9 and 10 or, respectively, 11 and 12 can be fashioned identically.

The dimensions $d_F$, $I_F$ that are selected for the different coil pairs 7 and 8, 9 and 10 and possibly 11 and 12 do not thereby need to coincide.

Figure 4B:
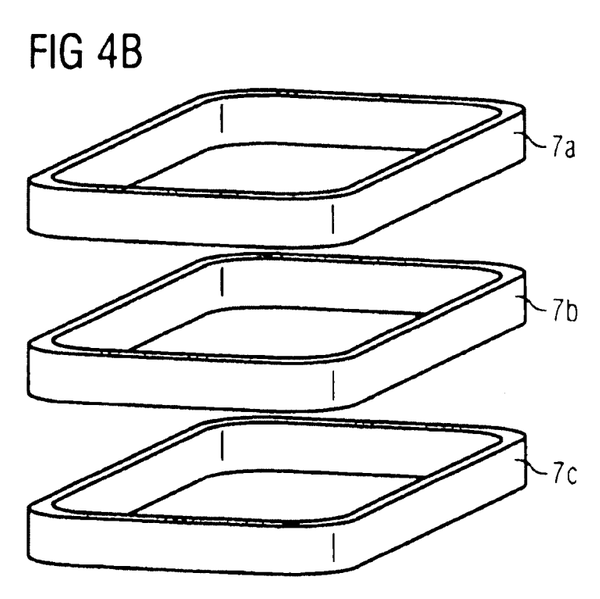
FIG. 4B illustrates a surface coil divided in sub-coils.

The surface coils 7-12 can respectively be divided into multiple individual sub-coils. Again in the example of the surface coil 7 of FIG. 4A, the surface coil 7 lying in the x-z-plane can be separated into sub-coils 7*a*, 7*b* and 7*c* lying atop one another in the y-direction (i.e. in the direction of the normal vector standing on the cross section surface of the coil 7), as is shown in FIG. 4*b*. The surface coil 8 would likewise accordingly be separated into sub-coils 8*a*, 8*b* and 8*c* (not shown). The dimensions of the sub-coils 7*a* and 8*a*, 7*b* and 8*b* and 7*c* and 8*c* advantageously coincide. A homogenization of the field gradients $\partial B_y/\partial x$ that can be generated by the surface coils 7 and 8 is advantageously achieved. An interstice on the order of 1 cm can thereby lie between two coils situated one atop the other. The remaining surface coils 9-12 can accordingly also be divided into multiple sub-coils, with the corresponding homogenization of their gradient fields. The division into more or fewer sub-coils than shown in FIG. 4B is likewise conceivable.

Figure 5A:
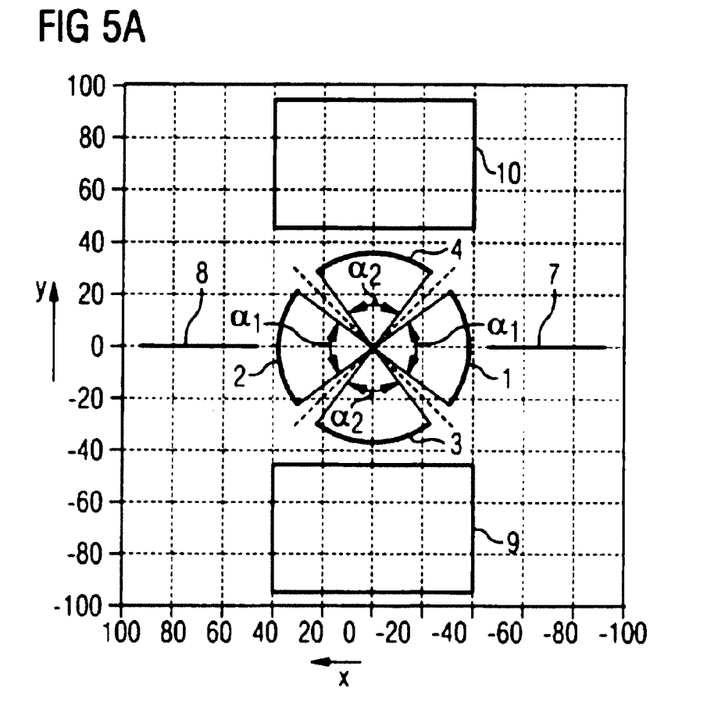
FIG. 5A is a cross-section through a coil arrangement according to the invention.

A further embodiment of the coil arrangement 100 according to FIG. 5A concerns only the saddle coils 1-4. The special embodiment of the saddle coils 1-4 can replace the saddle coils 1-4 contained within the scope of the exemplary embodiments described previously. The saddle coils 1-4 can be fashioned differently with regard to the solid angle α along the periphery of the surface shell. The first coil 1 and the second coil 2 respectively extend over a first solid angle $\alpha_1$ along the periphery of the surface shell while the third coil 3 and the fourth coil 4 respectively extend over a second solid angle $\alpha_2$. In order to amplify the magnetic field $B_y$ in the z-direction as well as the gradient field $\partial B_y/\partial y$, the solid angles $\alpha_2$ of the saddle coils 3 and 4 are increased to $\alpha_2 > 90°$. However, the solid angles advantageously lie in a range of $90° < \alpha_2 < 110°$. The first solid angle $\alpha_1$ of the saddle coils 1 and 2 is then to be reduced accordingly.

Figure 5B:
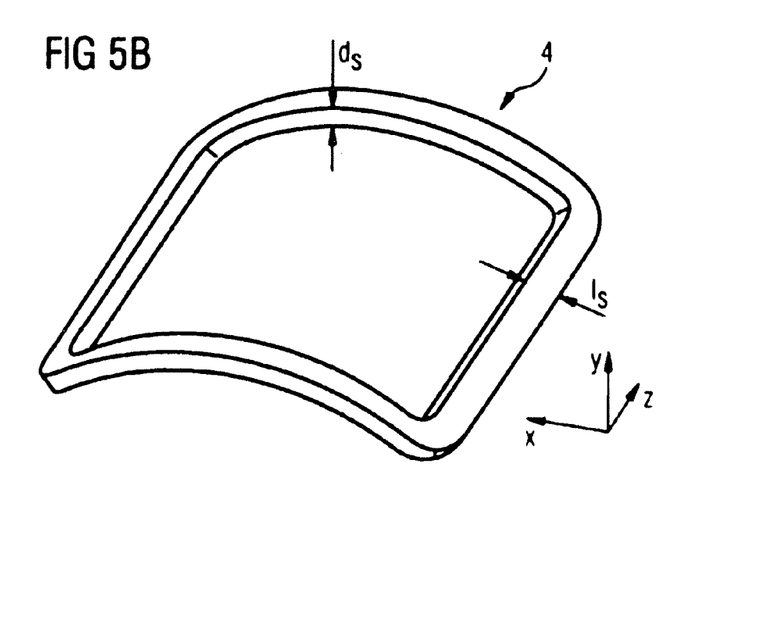
FIG. 5B illustrates a saddle coil in perspective view.

A preferred embodiment of the saddle coil 4 is shown in FIG. 5*b*. The remaining saddle coils can be dimensioned correspondingly. The saddle coil 4 is fashioned flat, meaning that the extent $d_S$ of the conductive segment in the radial direction can be smaller than the lateral extent $I_S$ of the conductive segment in, for example, the z-direction.

Figure 6:
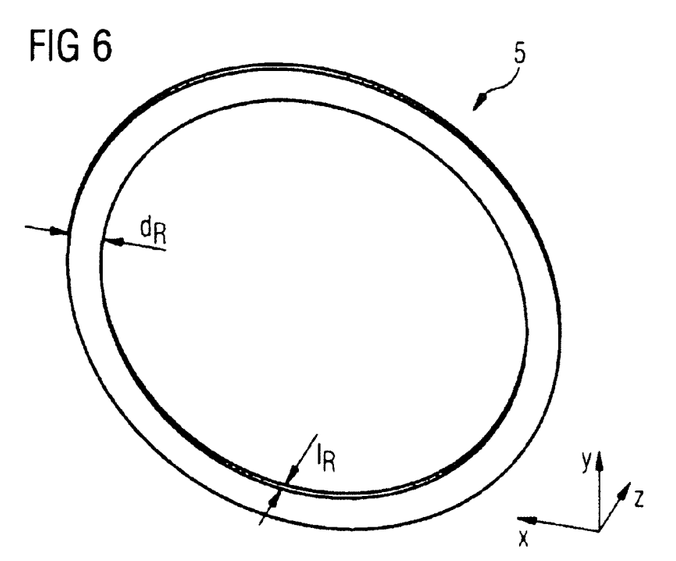
FIG. 6 illustrates a ring coil in perspective view.

FIG. 6 shows an embodiment of the ring coil 5 that is executed flat as viewed in the z-direction. This means that the extent $I_R$ in the z-direction can be smaller than the width $d_R$ of the ring, i.e. than the extent $d_R$ of the ring coil 5 in the radial direction. The ring coil 6 can be fashioned identically.

Figure 7:
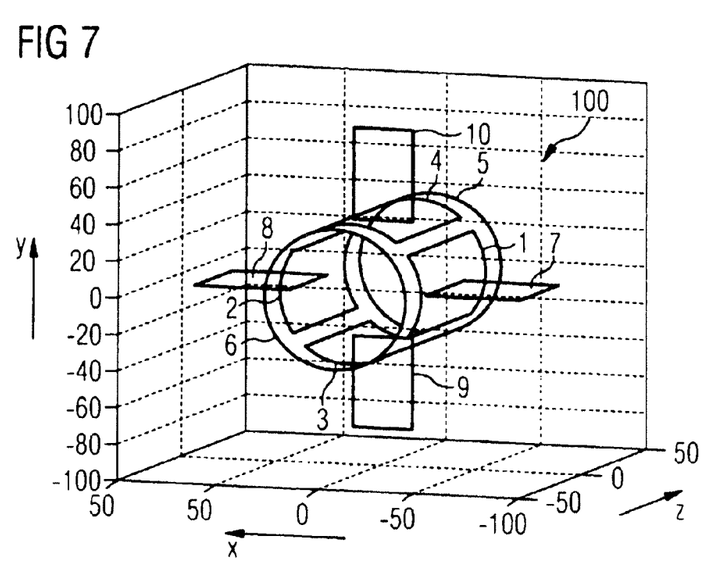
FIG. 7 schematically illustrates a further exemplary embodiment of the coil arrangement according to the invention.

In a further embodiment that is drawn in FIG. 7, the surface coils 7, 8 and/or 9, 10 are brought spatially closer to the work space A. This has the advantage that the gradient fields corresponding to the secondary diagonal elements of the gradient matrix G—in particular the gradient fields $\partial B_y/\partial x$ and/or $\partial B_x/\partial y$ in the present case—are amplified without more powerful electronics being required. For this the surface coils 7, 8 and/or 9, 10 are presently spatially integrated into the saddle coils so that at least the radially inner conductive segments of the surface coils 7, 8 and/or 9, 10 lie closer to the work space A. In contrast to the exemplary embodiments described above, the surface coils 7, 8 and/or 9, 10 are now no longer located completely radially outside of the surface shell of the cylinder formed by the saddle coils 1-3. For this the surface coils 7, 8 and/or 9, 10 must be shortened in the z-direction corresponding to the dimensioning of the saddle coils, which can entail the additional advantage that the weight of the surface coils 7, 8 and/or 9, 10 is reduced.

In addition to the number of individual coils to be used, the capsule magnetization direction and the operation of the individual coils as coil pairs or individually by power amplifiers, the exemplary embodiments described above also differ in that the concrete embodiments can vary with regard to the dimensions and the power requirement of the individual coils 1-10 or, respectively, 1-12.

In the exemplary embodiments with crossed coils that are shown in connection with FIGS. 1 and 3C, one of the crossed coils can respectively lie within the other coil, meaning that the inner coil must be designed correspondingly smaller than the outer, surrounding coil. Alternatively, the conducting segments can intersect, meaning that the conductor traces of the two coils can alternate at the intersection point of the coils.

It is noted that the above device of the coordinate system x, y, z is arbitrary, in particular concerning the alignment of the x-axis and the y-axis. A rotation of the coil arrangement 100 according to one of the exemplary embodiment described above by an arbitrary rotation angle around the longitudinal axis of the coil arrangement—i.e. around the z-axis of the coordinate system—is not additionally described but is likewise the subject matter of the present invention. This in particular pertains to the first exemplary embodiment and the fifth exemplary embodiment as well as their additional embodiments since all magnetic degrees of freedom can be generated with these. A rotation of the coil arrangement 100 by, for example, 90° around the z-axis produces a coil arrangement 100' with which all magnetic degrees of freedom can likewise be generated. The coil arrangement 100' accordingly works just like the coil arrangement 100.

Figure 8A:
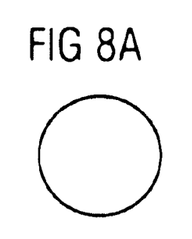
FIGS. 8A through 8E illustrate cylindrical cross-sections, in schematic form, of various embodiments of coils in accordance with the present invention.
Figure 8B:
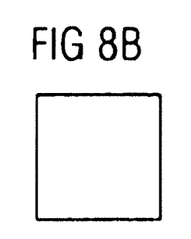
Figure 8C:
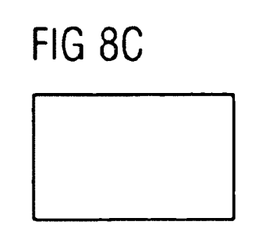
Figure 8D:
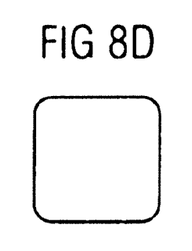
Figure 8E:
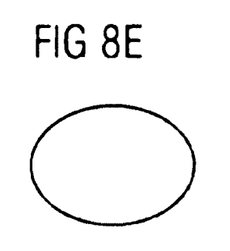
Figure 8F:
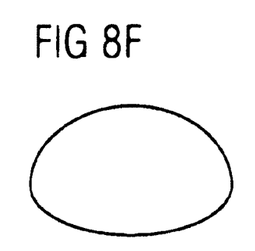

All described exemplary embodiments of the coil arrangements 100 contain four saddle coils 1-4 and two ring coils 5, 6 that all lie on the surface shell of a cylinder with circular cross section (schematically shown in FIG. 8A) or, respectively, describe the surface shell of a circular cylinder. Alternatively, however, these 6-coil cylinders can also possess a quadratic or rectangular cross section (FIGS. 8B, 8C). Instead of the four saddle coils and instead of the two ring coils, four flat coils and two rectangular coils are then used. Furthermore, the cross section of the cylinder can also be quadratic or rectangular with rounded corners, as indicated in FIG. 8D. An elliptical cross section (FIG. 8E) or an asymmetrical cross section (FIG. 8F) are also conceivable, for example a flattened circle. The cross section of the cylinder is realized by the shape of the individual coils 1-6.

In the case that a water cooling of individual coils is required, a cooling system can be provided via a hollow conduit through which water—not current—flows. For the ring coils 5, 6, the hollow conduit can lie as a winding layer on the outside of the winding package and can preferably be cast with the winding package. For the saddle coils 1-4, the cooling conduit winding layer can lie on the outside of the current-carrying winding package. Given the flat coils 7-10 or 7-12, a hollow conduit layer is advantageously first wound on the winding body and then the current-carrying rectangular conductor is wound on this.

Figure 9:
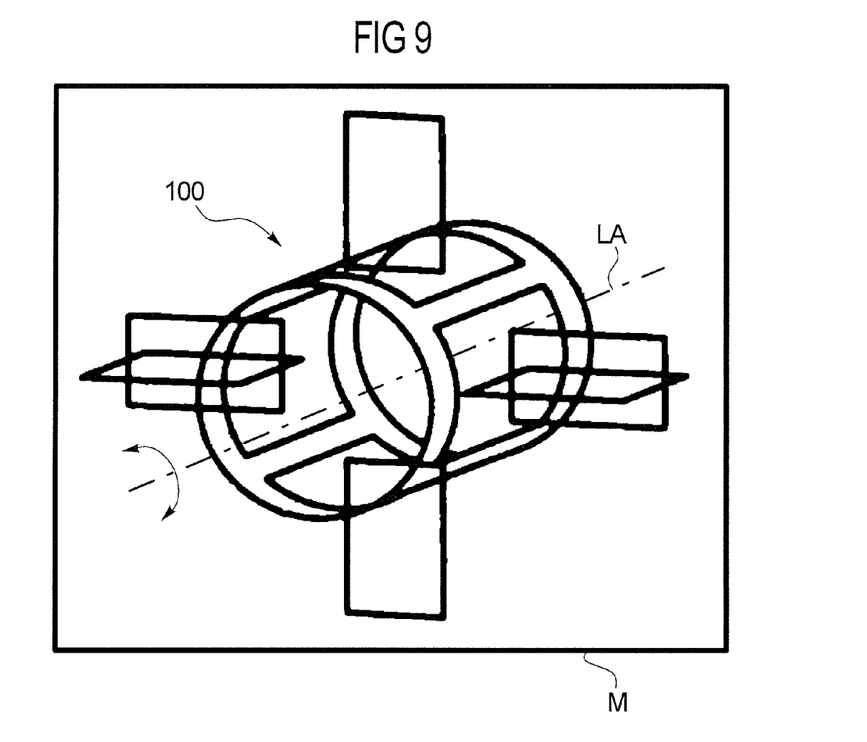
FIG. 9 schematically illustrates a mount allowing rotational movement of the entire coil arrangement.

FIG. 9 schematically illustrates a mount M for the coil arrangement 100 that allows rotation of the entire coil arrangement 100 around the longitudinal axis LA thereof, as schematically indicated by the curved double arrow.

Figure 10:
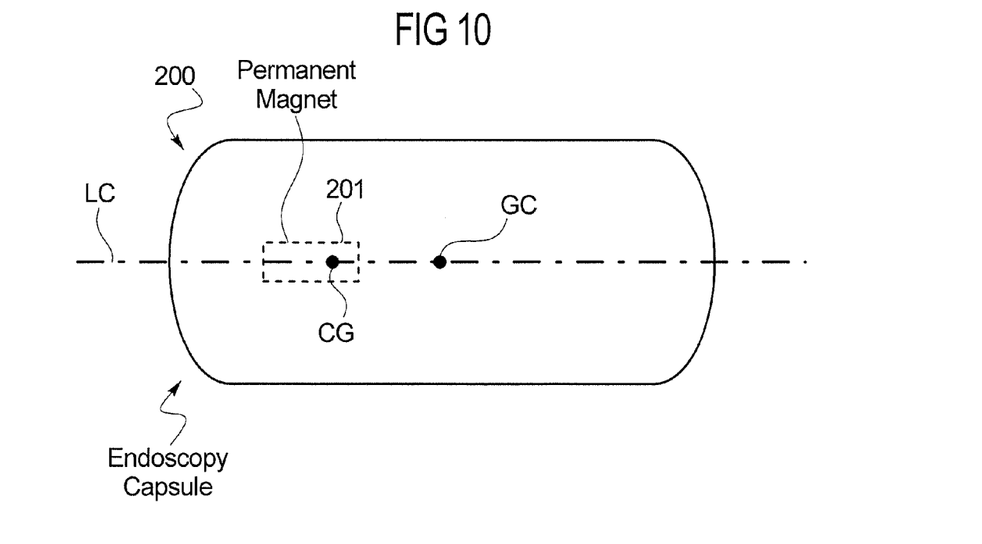
FIG. 10 schematically illustrates the magnetic element in the form of an endoscopy capsule.

FIG. 10 schematically illustrates the magnetic element in the form of the aforementioned endoscopy capsule 200, which has a capsule longitudinal axis LC. The endoscopy capsule 200 has a geometrical center GC that does not coincide with a center of gravity CG of the capsule 200. The endoscopy capsule 200 can contain a permanent magnetic 201 that, in the embodiment of FIG. 10, is oriented to give the endoscopy capsule 200 a magnetic dipole moment aligned paralleled to the longitudinal axis LC. In another embodiment, the permanent magnetic can be oriented so as to give the endoscopy capsule 200 a magnetic dipole moment aligned perpendicularly to the longitudinal axis LC.

Although modifications and changes may be suggested by those skilled in the art, it is the intention of the inventor to embody within the patent warranted heron all changes and modifications as reasonably and properly come within the scope of his contribution to the art.

I claim as my invention:

1. A coil arrangement comprising:
   multiple individual coils configured to generate a guide field in a workspace defined by a Cartesian coordinate system, said guide field being selected from the group consisting of a magnetic field formed by three individual field components respectively in the directions of said Cartesian coordinate system, and at least four independent gradient fields of a gradient matrix, said guide field being configured to guide a magnetic element therein in said workspace;
   said multiple independent coils comprising a plurality of first individual coils, a plurality of second individual coils, and a plurality of third individual coils;
   said plurality of first individual coils being arranged in series along a circumferential direction of a surface shell of an imaginary cylinder having a longitudinal cylinder axis extending along the Z-direction of said Cartesian coordinate system;
   said plurality of second individual coils being arranged at two opposite ends of said cylinder; and
   said plurality of third individual coils each having a cross-section with the cross-sections of the respective third individual coils being oriented as blades perpendicular to said longitudinal cylinder axis and projecting from an exterior of said imaginary cylinder.

2. A coil arrangement as claimed in claim 1 wherein said plurality of first individual coils, said plurality of second individual coils and said plurality of third individual coils form coil pairs, each coil pair comprising two of said individual coils located point-symmetrically relative to the origin of said Cartesian coordinate system, and said coil pairs respectively generating said components of said magnetic field or said four independent gradient fields of said gradient matrix.

3. A coil arrangement as claimed in claim 2 wherein said first plurality of individual coils comprise a first coil, a second coil, a third coil and a fourth coil, said first coil and said second coil forming a first coil pair and said third coil and said fourth coil forming a second coil pair.

4. A coil arrangement as claimed in claim 3 wherein each of said first, second, third and fourth coils has a cross-sectional coil surface with a geometric center point, and wherein the geometric center point of said first coil is on the negative x-axis of said Cartesian coordinate system, the geometric center point of the second coil is on the positive x-axis of said Cartesian coordinate system, the geometric center point of the third coil is on the negative y-axis of said Cartesian coordinate system, and the geometric center point of the fourth coil is on the positive y-axis of said Cartesian coordinate system, and wherein the respective cross-sectional surfaces of the first coil and the second coil are in planes parallel to the y-z plane of the Cartesian coordinate system, and the respective cross-sectional surfaces of the third coil and the fourth coil are in planes parallel to the x-z plane of the Cartesian coordinate system.

5. A coil arrangement as claimed in claim 3 wherein the first coil, the second coil, the third coil and the fourth coil each extend over respectively equal solid angles along the circumferential direction of said surface shell.

6. A coil arrangement as claimed in claim 3 wherein said first coil and said second coil each extend through a first solid angle along a circumferential direction of the surface shell, and the third coil and the fourth coil each extend through a second solid angle along the circumferential direction of the surface shell, said first solid angle being unequal to said second solid angle.

7. A coil arrangement as claimed in claim 6 wherein said second solid angle is larger than said first solid angle, and said second solid angle is in a range between 90° and 110°.

8. A coil arrangement as claimed in claim 4 wherein said plurality of second individual coils comprise a fifth coil and a sixth coil, forming a third coil pair.

9. A coil arrangement as claimed in claim 8 wherein each of said fifth coil and said sixth coil has a cross-sectional surface with a geometric center point, and wherein the geometric center point of the fifth coil is on the positive z-axis of said Cartesian coordinate system and the geometric center point of the sixth coil is on the negative z-axis of the Cartesian coordinate system, and wherein the respective cross-sectional surfaces of the fifth coil and the sixth coil are respectively in planes parallel to the x-y plane of the Cartesian coordinate system.

10. A coil arrangement as claimed in claim 9 wherein said plurality of third individual coils comprise a seventh coil, an eighth coil, a ninth coil and a tenth coil, said seventh and said eighth coil forming a fourth coil pair, and said ninth coil and said tenth coil forming a fifth coil pair.

11. A coil arrangement as claimed in claim 10 wherein said plurality of third individual coils comprise an eleventh coil and a twelfth coil, said eleventh coil and said twelfth coil forming a sixth coil pair.

12. A coil arrangement as claimed in claim 11 wherein each of said eleventh coil and said twelfth coil has a cross-sectional surface having a geometric center point, and wherein the geometric center point of the eleventh coil is on the negative x-axis of the Cartesian coordinate system and the geometric center point of the twelfth coil is on the positive x-axis of the Cartesian coordinate system, and the respective cross-sectional surfaces of the eleventh coil and the twelfth coil are in the x-y plane of the Cartesian coordinate system.

13. A coil arrangement as claimed in claim 12 wherein each of said seventh coil, said eighth coil, said ninth coil and said tenth coil has a cross-sectional surface with a geometric center point, and wherein the geometric center point of the seventh coil is on the negative x-axis of the Cartesian coordinate system, the geometric center point of the eighth coil is on the positive x-axis of the Cartesian coordinate system, the geometric center point of the ninth coil is on the negative y-axis of the Cartesian coordinate system, and the geometric center point of the tenth coil is on the positive y-axis of the Cartesian coordinate system, and wherein the respective cross-sectional surfaces of the seventh coil and the eighth coil are in the x-z plane of the Cartesian coordinate system, and the respective cross-sectional surfaces of the ninth coil and the tenth coil are in the x-y plane of the Cartesian coordinate system.

14. A coil arrangement as claimed in claim 13 wherein the respective positions of the geometric center points of the eleventh and the seventh coil are substantially congruent, and wherein the respective positions of the geometric center points of the twelfth coil and the eighth coil are substantially congruent.

15. A coil arrangement as claimed in claim 12 wherein each of said seventh coil, said eighth coil, said ninth coil and said tenth coil has a cross-sectional surface with a geometric center point, and wherein the geometric center point of the seventh coil is on the negative y-axis of the Cartesian coordinate system, the geometric center point of the eighth coil is on the positive y-axis of the Cartesian coordinate system, the geometric center point of the ninth coil is on the negative y-axis of the Cartesian coordinate system, and the geometric center point of the tenth coil is on the positive y-axis of the Cartesian coordinate system, and wherein the respective cross-sectional surfaces of the seventh coil and the eighth coil are in the y-z plane of the Cartesian coordinate system, and the respective cross-sectional surfaces of the ninth coil and the tenth coil are in the x-y plane of the Cartesian coordinate system.

16. A coil arrangement as claimed in claim 15 wherein the respective positions of the geometric center points of the ninth coil and the seventh coil are substantial congruent, and the respective positions of the geometric center points of the tenth coil and the eighth coil are substantially congruent.

17. A coil arrangement as claimed in claim 11 wherein each of said seventh coil, said eighth coil, said ninth coil, said tenth coil, said eleventh coil and said twelfth coil has a cross-sectional surface, and wherein said seventh coil and said eighth coil in said fourth coil pair, said ninth coil and said tenth coil in said fifth coil pair, and said eleventh coil and said twelfth coil in said sixth coil pair are, in the respective fourth, fifth and sixth coil pairs, arranged above each other in a direction of a vector normal to respective cross-sectionals surfaces, with a spacing therebetween.

18. A coil arrangement as claimed in claim 17 comprising:
a first power amplifier that supplies power to said first coil and said second coil;
a second power amplifier that supplies power to said seventh coil and said eighth coil;
a third power amplifier that supplies power to said ninth coil and said tenth coil;
a fourth power amplifier that supplies power to said eleventh coil and said twelfth coil; and
an additional power amplifier that supplies power to said third coil, said fourth coil, said fifth coil and said sixth coil.

19. A coil arrangement as claimed in claim 17, comprising:
a first power amplifier that supplies power to said first coil and said second coil;
a second power amplifier that supplies power to said fifth coil and said sixth coil;
a third power amplifier that supplies power to said seventh coil and said eighth coil;
a fourth power amplifier that supplies power to said ninth coil and said tenth coil; and
an additional power amplifier that supplies power to said third coil and said fourth coil.

20. A coil arrangement as claimed in claim 17, comprising:
a first power amplifier that supplies power to said first coil and said second coil;
a second power amplifier that supplies power to said seventh coil and said eighth coil;
a third power amplifier that supplies power to said ninth coil and said tenth coil; and
an additional power amplifier that supplies power to said third coil, said fourth coil, said fifth coil and said sixth coil.

21. A coil arrangement as claimed in claim 17, comprising:
a first power amplifier that supplies power to said third coil and said fourth coil;
a second power amplifier that supplies power to said seventh coil and said eighth coil;
a third power amplifier that supplies power to said ninth coil and said tenth coil; and
respective additional power amplifiers that supply power to said first coil, said second coil, said fifth coil and said sixth coil.

22. A coil arrangement as claimed in claim 1 wherein said plurality of first individual coils are respectively configured in coil configurations selected from the group consisting of a saddle coil configuration, a surface coil configuration, and a ring coil configuration.

23. A coil arrangement as claimed in claim 1 wherein said plurality of first individual coils are equally spaced apart around the circumferential direction of said surface shell.

24. A coil arrangement as claimed in claim 1 wherein said plurality of second individual coils are respectively configured in coil configurations selected from the group consisting of a ring coil configuration and a surface coil configuration.

25. A coil arrangement as claimed in claim 1 wherein said plurality of third individual coils are respectively configured in coil configurations selected from the group consisting of a ring coil configuration and a surface coil configuration.

26. A coil arrangement as claimed in claim 1 comprising a coil arrangement mount allowing rotation of all of said multiple individual coils, as a unit, around the z-axis of the Cartesian coordinate system.

27. A coil arrangement as claimed in claim 1 wherein said plurality of third individual coils comprises a subset of said plurality of third individual coils all oriented in a common plane that contains a circumference of said imaginary cylinder.

28. A coil arrangement as claimed in claim 1 wherein said plurality of third individual coils comprises a subset of said plurality of third individual coils all oriented in a plane that is perpendicular to a circumference of said imaginary cylinder.

29. A coil arrangement as claimed in claim 1 wherein said plurality of third individual coils comprises a first subset of said plurality of third individual coils all oriented in a common plane that contains a circumference of said imaginary cylinder, and a second subset of said plurality of third individual coils all oriented in a plane that is perpendicular to said circumference of said imaginary cylinder.

30. An endoscopy system comprising:
an endoscopy capsule having a magnetic dipole moment;
multiple individual coils configured to generate a guide field in a workspace defined by a Cartesian coordinate system, said guide field being selected from the group consisting of a magnetic field formed by three individual field components respectively in the directions of said Cartesian coordinate system, and at least four independent gradient fields of a gradient matrix, said guide field being configured to interact with said magnetic dipole moment to guide said endoscopy capsule therein in said workspace;
said multiple independent coils comprising a plurality of first individual coils, a plurality of second individual coils, and a plurality of third individual coils;
said plurality of first individual coils being arranged in series along a circumferential direction of a surface shell of an imaginary cylinder having a longitudinal cylinder axis extending along the Z-direction of said Cartesian coordinate system;
said plurality of second individual coils being arranged at two opposite ends of said cylinder; and
said plurality of third individual coils each having a cross-section with the cross-sections of the respective third individual coils being oriented as blades perpendicular to said longitudinal cylinder axis and projecting from an exterior of said imaginary cylinder.

31. A coil arrangement as claimed in claim 30 wherein said magnetic element is an endoscopy capsule having a magnetic dipole moment aligned parallel to a longitudinal axis of the endoscopy capsule.

32. A coil arrangement as claimed in claim 30 wherein said magnetic element is an endoscopy capsule having a magnetic dipole moment aligned perpendicularly to a longitudinal axis of the endoscopy capsule.

33. A coil arrangement as claimed in claim 30 wherein said magnetic element comprises an endoscopy capsule having a longitudinal axis, with a permanent magnet rigidly mounted therein with poles of said permanent magnet oriented parallel to perpendicular to said longitudinal axis.

34. A coil arrangement as claimed in claim 30 wherein said magnetic element has a center of gravity that does not coincide with a geometric center of said magnetic element along a longitudinal axis of the magnetic element.

* * * * *